United States Patent
Aizawa et al.

(10) Patent No.: US 9,726,605 B2
(45) Date of Patent: Aug. 8, 2017

(54) FLUORESCENCE IMMUNO-CHROMATOGRAPHY, KIT AND TEST STRIP FOR THE SAME

(71) Applicant: FURUKAWA ELECTRIC CO., LTD., Tokyo (JP)

(72) Inventors: Hideki Aizawa, Tokyo (JP); Michio Ohkubo, Tokyo (JP)

(73) Assignee: FURUKAWA ELECTRIC CO., LTD., Tokyo (JP)

( * ) Notice: Subject to any disclaimer, the term of this patent is extended or adjusted under 35 U.S.C. 154(b) by 1183 days.

(21) Appl. No.: 13/830,435

(22) Filed: Mar. 14, 2013

(65) Prior Publication Data

US 2014/0273271 A1    Sep. 18, 2014

(51) Int. Cl.
| | |
|---|---|
| *G01N 31/00* | (2006.01) |
| *G01N 33/53* | (2006.01) |
| *G01N 21/64* | (2006.01) |
| *G01N 33/543* | (2006.01) |
| *G01N 33/558* | (2006.01) |
| *G01N 21/84* | (2006.01) |

(52) U.S. Cl.
CPC ..... *G01N 21/6428* (2013.01); *G01N 21/8483* (2013.01); *G01N 33/54373* (2013.01); *G01N 33/558* (2013.01)

(58) Field of Classification Search
None
See application file for complete search history.

(56) References Cited

U.S. PATENT DOCUMENTS

| | | | |
|---|---|---|---|
| 8,110,349 B2 * | 2/2012 | Cohen .............. | G01N 33/54373 422/50 |
| 2004/0029177 A1 | 2/2004 | Nadaoka et al. | |
| 2009/0068639 A1 | 3/2009 | Aizawa et al. | |
| 2009/0215096 A1 | 8/2009 | Aizawa et al. | |
| 2011/0171749 A1 * | 7/2011 | Alocilja .................. | B82Y 5/00 436/501 |
| 2011/0244597 A1 | 10/2011 | Tsukada et al. | |

FOREIGN PATENT DOCUMENTS

| | | |
|---|---|---|
| JP | 2010-197248 A | 9/2010 |
| WO | WO 03/014740 A1 | 2/2003 |
| WO | WO 2007/097377 A1 | 8/2007 |
| WO | WO 2008/018566 A1 | 2/2008 |
| WO | WO 2010/061772 A1 | 6/2010 |

OTHER PUBLICATIONS

Gottfried et al. (Abstracts, 58th Southesat Regional Meeting of the American Chemical Society, 2006, SRM06-101).*
Japanese Office Action for Japanese Application No. 2011-221169, dated Nov. 12, 2013.

* cited by examiner

*Primary Examiner* — Lisa Cook
(74) *Attorney, Agent, or Firm* — Birch, Stewart, Kolasch & Birch, LLP

(57) ABSTRACT

The invention is directed to a fluorescence immunochromatography method carried out by illuminating a fluorescent substance in a membrane with excitation light and detecting fluorescence emitted from the fluorescent substance, by applying a sample to a test strip having a membrane and a transparent film attached to the surface of the membrane, wherein the transparent film satisfies Formula (1) Formula (1) $n_{Ff} > n_{Wf}$ ($n_{Ff}$: refractive index of transparent film at wavelength $\lambda^f$ of the fluorescence) ($n_{Wf}$: refractive index of analyte liquid at wavelength $\lambda^f$ of the fluorescence), and wherein the membrane contains a fluorescent labeling reagent which binds to target substance contained in the sample; binding the fluorescent labeling reagent to the target substance; immobilizing the fluorescent labeling reagent bound to the target substance in the membrane; detecting the presence of target substance.

10 Claims, 4 Drawing Sheets
(2 of 4 Drawing Sheet(s) Filed in Color)

FLUORESCENCE IMMUNO-CHROMATOGRAPHY, KIT AND TEST STRIP FOR THE SAME

TECHNICAL FIELD

The present invention relates to fluorescence immunochromatography, and a kit and a test strip for the same.

BACKGROUND ART

An immunochromatography (hereinafter, it may be referred to as immunochromato-method) is a diagnostic method using nanoparticles. Being simple to operate and requiring relatively short time of approximately 10 to 30 minutes and no expensive devices for determination, it is widely used as an excellent simple diagnostic method in actual clinical areas. For example, for determination of influenza virus infection, by having a pharynx cotton swab or nasal cavity cotton swab collected from a patient as an analyte, the determination can be made on site within a short time, and thus it is used as a very dominant tool for quick determination of infection.

Colored particles such as gold colloid or colored latex particles are generally used as labeling particles for immunochromatography. However, immunochromatography using colored particles has poor sensitivity, and thus it cannot be used for a test subject containing insufficient amount of a test substance in an analyte. Further, for determination of influenza virus detection, initial stage of infection having no sufficient amount of viruses in an analyte may be found to be negative by immunochromatography using colored particles. For solving these problems, it has been tried to achieve highly sensitive immunochromatography.

As a method of achieving highly sensitive immunochromatography, there is "fluorescence immunochromatography" which uses fluorescent particles as labeling particles (see, WO 2008/018566 A, WO 2007/097377 A and JP-A-2010-197248 A). According to fluorescence immunochromatography, fluorescent lines are detected by using latex particles, silica particles, or semi-conductor nanoparticles having fluorescent characteristics as labeling particles, and therefore highly sensitive determination can be made compared to a naked eye determination of immunochromatography which uses colored particles.

CITATION LIST

Patent Document

{Patent Document 1} WO2008/018566 pamphlet
{Patent Document 2} WO2007/097377 pamphlet
{Patent Document 3} JP-A-2010-197248

DISCLOSURE OF INVENTION

The present invention relates to the following aspects.

An immunochromatography carried out by illuminating a fluorescent substance in a membrane with excitation light and detecting fluorescence emitted from the fluorescent substance, the immunochromatography comprising the steps of:

preparing a membrane having a transparent film, the transparent film being closely attached to the surface of the membrane, the transparent film satisfying a specific property related to a refractive index with respect to analyte liquid;

illuminating a fluorescent substance in the membrane with excitation light through the transparent film, thereby bringing fluorescence components into a guided wave of the transparent film, the fluorescence components being included in the fluorescence incident to the transparent film, the fluorescence components having an incident angle exceeding a critical angle, the fluorescence being wave guided by virtue of the fluorescence components totally reflected (totally internal reflected) on the interface between the transparent film and the air and on the surface of the membrane, the membrane being closely attached to the surface of the transparent film; and detecting another fluorescence components not exceeding the critical angle, the another fluorescence components being included in the fluorescence emitted from the fluorescent substance, the detection being made by virtue of the fluorescence components passing through the film.

Other and further features and advantages of the invention will appear more fully from the following description, appropriately referring to the accompanying drawings.

BRIEF DESCRIPTION OF DRAWINGS

The patent or application file contains at least one color drawing. Copies of this patent or patent application publication with color drawing will be provided by the USPTO upon request and payment of the necessary fee.

FIGS. 2A and 2B are diagrams illustrating the immunochromatography membrane preferably used in the invention, in which FIG. 2A is a plan view and FIG. 2B is an expanded cross-sectional view.

BEST MODE FOR CARRYING OUT THE INVENTION

Figure 1:
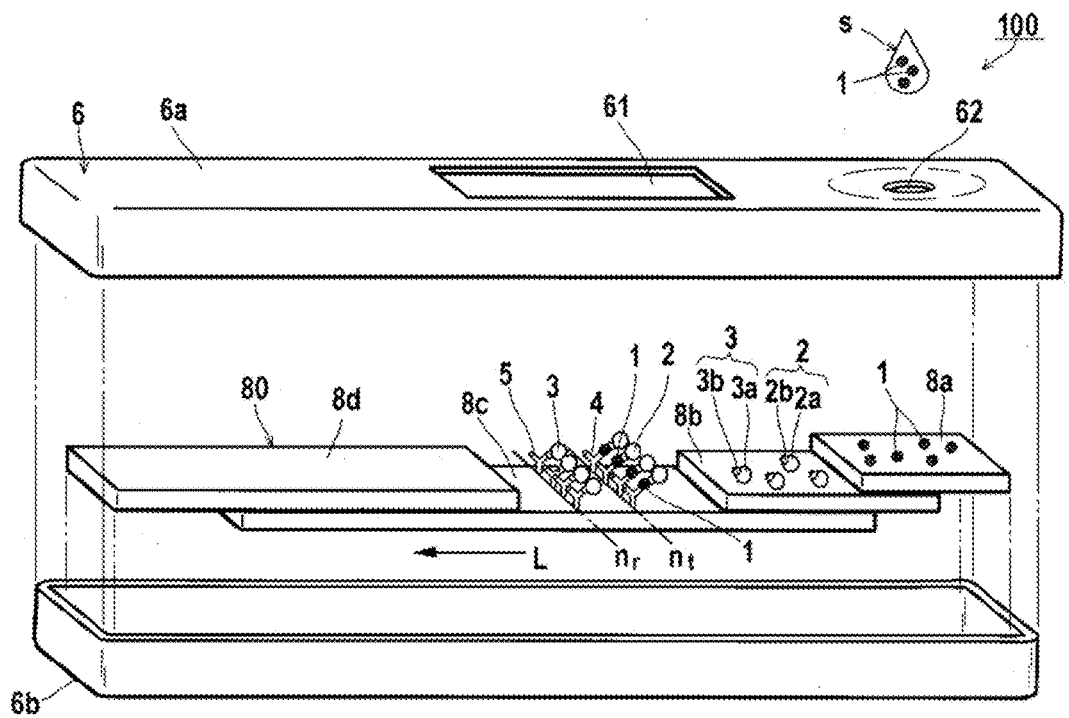
FIG. 1 is an exploded perspective view schematically illustrating the test stick as a preferred embodiment of the invention.

As described above, although fluorescence immunochromatography is a method enabling excellent detection with high sensitivity, it was found to have problems as follows according to further studies.

The immunochromatography can be used for quick diagnosis. For example, detection can be made within 10 minutes. In such case, a membrane formed with a detection part is in a wet state. According to fluorescence immunochromatography, when a wet membrane is illuminated with excitation light, the illuminated excitation light and fluorescence scatted from fluorescent particles come into the whole membrane, yielding an entirely gleaming membrane (see, FIG. 6). As a result, the fluorescence-emitting line is overwhelmed by the entirely gleaming membrane, making it difficult to perform detection. Such phenomenon is a unique problem occurring in fluorescence immunochromatography which involves line detection based on light luminescence of labeling particles. That however does not occur in conventional immunochromatography, since line determination is performed by coloration of labeling particles, i.e., light absorption.

In view of the aspects described above, the present invention addresses to the provision of fluorescence immunochromatography which enables good determination even in a wet membrane state while smearing or blur in fluorescence detection line is suppressed. Further, the present invention addresses to the provision of a kit and a test strip that are used for the above fluorescence immunochromatography.

To solve the problems described above, inventors of the present invention conducted intensive studies. As a result, it was found that a phenomenon of having excitation light and fluorescence coming to a whole wet membrane can be suppressed by forming a specific layer of an optical film on the surface of the membrane. Consequently, the inventive fluorescence immunochromatography enables quick and highly sensitive determination can be achieved. The present invention is completed based on those findings.

Thus, the present invention provides the following means.
{1} An immunochromatography carried out by illuminating a fluorescent substance in a membrane with excitation light and detecting fluorescence emitted from the fluorescent substance, the immunochromatography having the steps of:

preparing a membrane having a transparent film, the transparent film being closely attached to the surface of the membrane, the transparent film satisfying following Formula (1) related to a refractive index with respect to analyte liquid;

illuminating a fluorescent substance in the membrane with excitation light through the transparent film, thereby bringing fluorescence components into a guided wave of the transparent film, the fluorescence components being included in the fluorescence incident to the transparent film, the fluorescence components having an incident angle exceeding a critical angle, the fluorescence being wave guided by virtue of the fluorescence components totally reflected on the interface between the transparent film and the air and on the surface of the membrane, the membrane being closely attached to the surface of the transparent film; and detecting another fluorescence components not exceeding the critical angle, the another fluorescence components being included in the fluorescence emitted from the fluorescent substance, the detection being made by virtue of the fluorescence components passing through (transmitting) the film.

$$n_{Ff} > n_{Wf} \quad \text{Formula (1)}$$

($n_{Ff}$: refractive index of transparent film at wavelength $\lambda^f$ of the fluorescence)
($n_{Wf}$: refractive index of analyte liquid at wavelength $\lambda^f$ of the fluorescence)

{2} The fluorescence immunochromatography according to {1}, wherein, as for the transparent film, a film satisfying following Formula (2) related to a refractive index with respect to analyte liquid is applied $$n_{Ff} > n_{Wf} + 0.1 \quad \text{Formula (2)}$$

($n_{Ff}$ and $n_{Wf}$ have the same meanings as defined in Formula (1)).

{3} The fluorescence immunochromatography according to {1} or {2}, wherein both the light transmittance ($T_{Fe}$) for wavelength $\lambda^e$ of the excitation light and the light transmittance ($T_{Ff}$) for wavelength $\lambda^f$ of the fluorescence of the transparent film are 80% or higher.

{4} A test strip according to any one of {1} to {3}, wherein the contact angle of water on the transparent film is 50° or more.

{5} The fluorescence immunochromatography according to any one of {1} to {4}, wherein fluorescent silica particles containing the fluorescent substance introduced to silica are used.

{6} The fluorescence immunochromatography according to any one of {1} to {5}, wherein the wavelength $\lambda^e$ of the excitation light is between 300 nm and 700 nm, and wherein the wavelength $\lambda^f$ of the fluorescence is between 350 nm and 800 nm.

{7} The fluorescence immunochromatography according to any one of {1} to {6}, wherein the wavelength $\lambda^e$ of the excitation light is between 500 nm and 550 nm, and wherein the wavelength $\lambda^f$ of the fluorescence is between 530 nm and 580 nm.

{8} The fluorescence immunochromatography according to any one of {1} to {7}, wherein the fluorescence incident to the transparent film and diffused therein is totally reflected on the interface between the transparent film and the air and on the interface between the transparent film and the membrane so that the transparent film becomes a waveguide, which suppresses the fluorescence from being diffused in the membrane and increases detectability of the fluorescence near the fluorescent substance.

{9} The fluorescence immunochromatography according to any one of {1} to {8}, wherein the excitation light is illuminated from a laser diode or a light emitting diode while a device for detecting only the fluorescence by removing the excitation light using an optical filter is used.

{10} The fluorescence immunochromatography according to any one of {1} to {9}, wherein the detection determination is made within 5 minutes.

{11} A kit used for immunochromatography to be carried out by illuminating a fluorescent substance with excitation light and detecting fluorescence emitted from the fluorescent substance, the kit having a test strip and a fluorescent substance, the test strip having a transparent film and a membrane main body for the transparent film being applied, the fluorescent substance for being added onto the membrane main body, the transparent film having a refractive index satisfying following Formula (1) with respect to analyte liquid, thereby bringing the fluorescence incident to the transparent film into a guided wave of the transparent film, the fluorescence being wave guided by virtue of the fluorescence components totally reflected on the interface between the transparent film and the air and on the surface of the membrane, the membrane being closely attached to the surface of the transparent film.

$$n_{Ff} > n_{Wf} \quad \text{Formula (1)}$$

($n_{Ff}$: refractive index of transparent film at wavelength $\lambda^f$ of the fluorescence)
($n_{Wf}$: refractive index of analyte liquid at wavelength $\lambda^f$ of the fluorescence)

{12} The kit according to {11}, further having labeled a silica particle as a labeling reagent, the labeled silica particles being formed from a silica particle containing a fluorescent substance therein.

{13} The kit according to {11} or {12}, wherein the transparent film has a thickness of between 20 μm and 1 mm.
{14} The kit according to any one of {11} to {13}, wherein the material of the transparent film is at least one selected from polyvinylidene fluoride, cellulose acetate, polymethyl methacrylate, polypropylene, nylon, polyethylene, polyvinyl chloride, polystyrene, polyvinylidene chloride, and polyethylene terephthalate to satisfy Formula (1) in correspondence with a refractive index of analyte liquid.
{15} A test strip used for immunochromatography to be carried out by illuminating a fluorescent substance with excitation light and detecting fluorescence emitted from the fluorescent substance, the test strip having a transparent film and a membrane main body for the transparent film being applied, the transparent film having a refractive index satisfying following Formula (1) with respect to analyte liquid, thereby bringing the fluorescence incident to the transparent film into a guided wave of the transparent film, the fluorescence being wave guided by virtue of the fluorescence components totally reflected on the interface between the transparent film and the air and on the surface of the membrane, the membrane being closely attached to the surface of the transparent film.

$$n_{Ff} > n_{Wf} \quad \text{Formula (1)}$$

($n_{Ff}$: refractive index of transparent film at wavelength $\lambda^f$ of the fluorescence)
($n_{Wf}$: refractive index of analyte liquid at wavelength $\lambda^f$ of the fluorescence)
{16} The test strip according to {15}, wherein the fluorescent substance is introduced to the silica particles.
{17} The test strip according to {15} or {16}, wherein the transparent film has a thickness of between 20 μm and 1 mm.
{18} The test strip according to any one of {15} to {17}, wherein the material of the transparent film is at least one selected from polyvinylidene fluoride, cellulose acetate, polymethyl methacrylate, polypropylene, nylon, polyethylene, polyvinyl chloride, polystyrene, polyvinylidene chloride, and polyethylene terephthalate.

As one example of a method for detecting a target substance according to the invention (i.e., immunochromatography), a preferred embodiment of a method for detecting a target substance by using a test strip for immunochromatography will be described.

[Test Strip]

In the test strip for immunochromatography according to the present embodiment, it is preferable that the following members be connected to each other in series so as to have a capillary phenomenon.

a member 8a for sample addition (sample pad)
a member 8b obtained by impregnation with silica nanoparticles (fluorescent labeling unit) 2, 3 as labeling reagent of the invention and drying them (conjugate pad)
a membrane 8c having an antibody immobilizing part (antibody immobilizing membrane)
an absorption pad 8d

Figure 2:
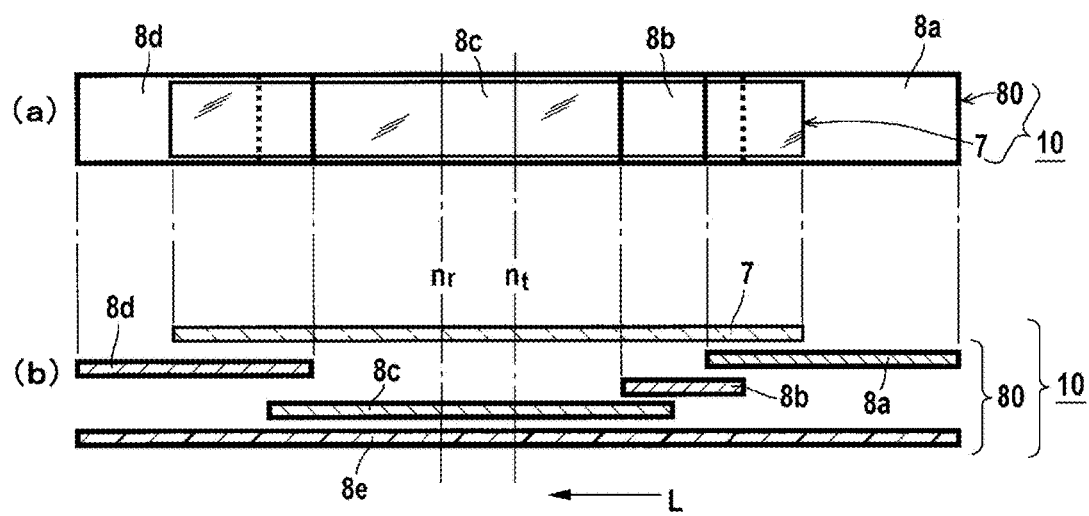

According to the present embodiment, a test strip 10 equipped with a main body of the above-described planar test piece (i.e., membrane main body) 80 is sandwiched between an upper casing part 6a and a lower casing part 6b to form a long test piece 100 as illustrated in FIG. 1 and FIGS. 2A and 2B. On the upper casing part 6a, a detection opening 61 and an opening 62 for introducing an analyte are provided. Through the detection opening 61, irradiation light is supplied to the membrane main body 80 present inside, and the fluorescence emitted therefrom can be collected, detected, and measured. Meanwhile, by supplying analyte liquid s to main body of the membrane 80 through the opening 62 for introducing an analyte, measurement test can be carried out.

A preferred embodiment of the test strip for immunochromatography is described in view of FIGS. 2A and 2B. However, it is evident that the invention is not limited to them. Further, the size ratio of each member is slightly different in FIGS. 2A and 2B compared to those described in FIG. 1, and a transparent film 7 and a backing sheet 8e are illustrated in FIGS. 2A and 2B without omitting them. FIG. 2A illustrates a plan view of a preferred embodiment of the test strip for immunochromatography of the invention, and FIG. 2B is an expanded longitudinal cross-sectional view of the test strip for immunochromatography illustrated in FIG. 1A. The test strip 10 for immunochromatography according to the present embodiment is provided with the sample pad 8a, the conjugate pad 8b, the antibody immobilizing membrane 8c, and the absorption pad 8d as described above. Further, like the present embodiment, it is preferable that each constitutional member be lined with the backing sheet 8e that is added with adhesives.

(Target Substance)

In the present invention, target substance 1 of the subject of detection and quantification includes include antigens, antibodies, DNAs, RNAs, sugars, polysaccharides, ligands, receptors, peptides, chemical substances and the like. In the present invention, a sample containing target substance 1 is no particularly limited, but the sample includes urine, blood, and so on.

(Sample Pad)

The sample pad 8a is a constitutional member to which a sample containing a target substance is loaded. Materials or the size of the sample pad is not specifically limited. Those commonly used for a product of the same type can be used.

(Conjugate Pad)

The conjugate pad 8b is a constitutional member impregnated with the labeling reagent silica nanoparticles (fluorescent labeling unit) 2, 3, in which a target substance included in a sample, which migrates from the sample pad 8a based on capillary phenomenon, is captured and labeled by the labeling reagent silica nanoparticles (labeling unit) as a result of a specific molecular recognition reaction such as antigen and antibody reaction.

The content of the labeling reagent silica nanoparticles (labeling unit) per unit area ($cm^2$) of the conjugate pad 8b is, although not particularly limited, preferably 1 μg to 100 μg. Examples of the impregnation method include a method of coating dispersion of the labeling reagent silica nanoparticles, applying or spraying, and then drying.

(Antibody Immobilizing Membrane)

In an antibody immobilizing part of the antibody immobilizing membrane 8c, a test line $n_t$ immobilized with an antibody for capturing a target substance to determine presence or absence of a target substance, i.e., to determine a positive response or a negative response, is formed. Preferably, the antibody immobilizing membrane 8c has a control line $n_r$ immobilized with an antibody for capturing the labeling reagent silica nanoparticles.

The membrane 8c is a constitutional member in which a target substance 1 labeled with the labeling reagent silica nanoparticles (labeling unit) 2 and 3 migrates according to capillary phenomenon, and it includes an antibody immobilizing part (determination part) in which a reaction of forming a sandwich type immunocomplex consisting of immobilized antibody—target substance—labeling reagent silica nanoparticles occurs. The shape of the antibody immobilizing part (determination part) in the membrane is not particularly limited as long as a capturing antibody is locally immobilized, and examples thereof include a line shape, a circular shape, a band shape, or the like. The line shape is preferable, and the line shape with width of 0.5 to 1.5 mm is more preferable.

According to a reaction of forming sandwich type immunocomplex consisting of immobilized antibody—target substance—labeling reagent silica nanoparticles (fluorescent labeling unit), the labeled target substance is captured by the antibody immobilizing part (determination part). Depending on level of labeling, determination of presence or absence of a target substance, i.e., determination of a positive response or a negative response, can be made. Specifically, as the labeling reagent silica nanoparticles (labeling unit) are concentrated on the antibody immobilizing part (determination part) and fluorescence is emitted around the fluorescent substance, detection and determination can be made by a naked eye or using a device for detection.

For fully completing the reaction of forming sandwich type immunocomplex or avoiding an influence of label such as a colored or fluorescent substance in a liquid sample on measurement or an influence of a labeling unit not bound to the target substance on measurement, it is preferable that the determination part of the antibody immobilizing membrane be formed such that it is somewhat distant from the connection end to the conjugate pad and the connection end to the absorption pad (for example, in the middle of the membrane or so).

Although the antibody immobilization amount in the antibody immobilizing part (test region) nt is not particularly limited, when it has a line shape, it is preferably 0.5 μg to 5 μg per unit length (cm). Examples of the immobilization method include a method of coating an antibody solution, applying or spraying, drying, and immobilizing by physical adsorption. To avoid an influence of non-specific adsorption on measurement after antibody immobilization described above, the entire antibody immobilizing membrane is preferably subjected to so-called blocking treatment in advance. For example, a method of impregnating in a buffer solution containing blocking agent such as albumin, casein, and polyvinyl alcohol for an appropriate time followed by drying can be mentioned. Examples of a commercially available blocking agent include skim milk (manufactured by DIFCO) and 4% Block Ace (trade name, manufactured by Meiji Dairies Corporation).

The membrane 8c also includes a reference region nr, in which fluorescent particles (labeling unit) 3 not captured by a target substance are captured. Accordingly, presence or absence, or amount against the target substance can be fixed compared to fluorescence from the test region nt. To have such activity, the fluorescent labeling unit 2 for test consists of fluorescent silica particles 2a and a test use binding substance 2b. The test use binding substance 2b has a binding property for a target substance. Meanwhile, the labeling unit 3 for reference consists of fluorescent silica particles 3a and a reference use binding substance 3b. The reference use capturing and binding substance has no binding property for a target substance but has binding property for a reference use capturing substance.

(Absorption Pad)

The absorption pad 8a is a constitutional membrane for absorbing an analyte S (target substance) which migrates along the membrane based on capillary phenomenon and also the labeling reagent silica nanoparticles (labeling unit) 2, 3 and generating a constant flow of them at all times.

The material of each of the aforementioned constitutional members is not particularly limited. Instead, members used for a test strip for immunochromatography can be used. Preferred examples of the sample pad and conjugated pad include a pad of glass fiber such as Glass Fiber Conjugate Pad (trade name, manufactured by MILLIPORE). Preferred examples of the membrane include a nitrocellulose membrane such as Hi-Flow Plus120 (trade name, manufactured by MILLIPORE), and preferred examples of the absorption pad include a cellulose membrane such as Cellulose Fiber Sample Pad (trade name, manufactured by MILLIPORE).

Examples of the backing sheet added with adhesives include AR9020 (trade name, manufactured by Adhesives Research).

[Transparent Film]

When a transparent film is applied to the membrane main body for the fluorescence immunochromatography of the invention, those satisfying the following relation are used.

$$n_{Ff} > n_{Wf} \qquad \text{Formula (1)}$$

($n_{Ff}$: refractive index of transparent film at wavelength $\lambda^f$ of the fluorescence)

($n_{Wf}$: refractive index of analyte liquid at wavelength $\lambda^f$ of the fluorescence)

Further, when there are plural wavelengths of excitation light or fluorescence, it means the wavelength with the highest luminance. When there is a luminance distribution, the wavelength exhibiting the highest peak is used for evaluation.

Further, with regard to excitation light, it is preferable that the following refractive index relation be satisfied for the transparent film and analyte liquid.

$$n_{Fe} > n_{We} \qquad \text{Formula (1)}$$

($n_{Fe}$: refractive index of transparent film at wavelength $\lambda e$ of excitation light)

($n_{We}$: refractive index of analyte liquid at wavelength $\lambda e$ of excitation light)

For example, when fluorescence wavelength is 589.3 nm ($\lambda^\circ$), since the refractive index of water at that wavelength is 1.333, it is required for the transparent film 7 used in the invention to have a refractive index of greater than 1.333. Further, when water (analyte liquid) is used as a medium, it is known that the refractive index has weak wavelength dependency and difference in the refractive index in the visible light range is 0.01 or so, because light of visible light range shows normal distribution.

There is a case in which wavelength dependency is not so high not only for a refractive index of water but also for a refractive index of film. Even in such case, it is meaningful to define a refractive index for each wavelength, and by having specific relation between a refractive index of the film and analyte liquid for fluorescence wavelength, the effect of the invention, i.e., suppressing bleeding or blur on detection, can be suitably exhibited.

According to the fluorescence immunochromatography of the invention, the refractive index under the aforementioned conditions is higher by 0.1 or more than the refractive index of the analyte liquid. More preferably, it is higher by 0.2 or more. It may be represented by the following relation. It is preferable to satisfy Formula (2). It is more preferable to satisfy Formula (3). In addition, $n_{Ff}$ and $n_{Wf}$ have the same meanings as defined for Formula (1).

$$n_{Ff} > n_{Wf} + 0.1 \qquad \text{Formula (2)}$$

$$n_{Ff} > n_{Wf} + 0.2 \qquad \text{Formula (3)}$$

Figure 4:
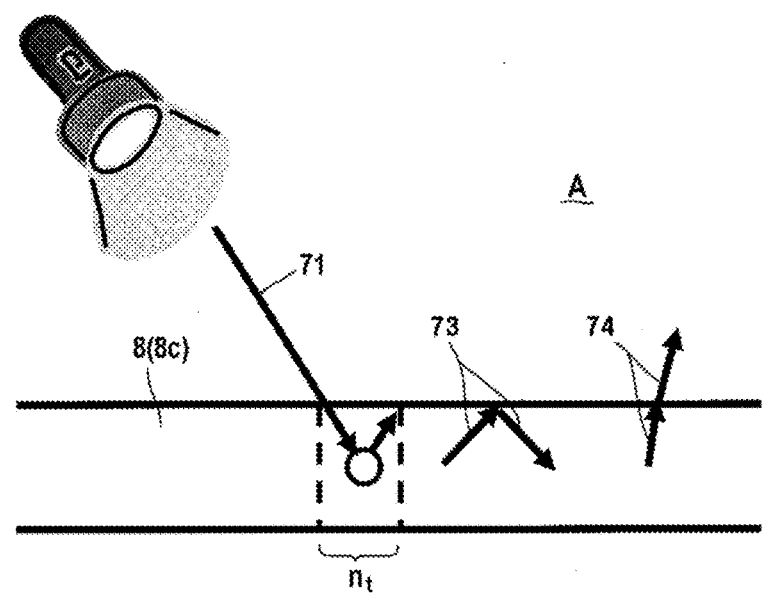
FIG. 4 is a diagram schematically illustrating reflection mechanism of excitation light and fluorescence according to conventional fluorescence immunochromatography based on a cross section of the membrane.

FIG. 4 schematically illustrates the detection state in a conventional test strip by way of a cross section of the membrane. Specifically, the detection state in the test region $n_t$ (i.e., near the fluorescent substance) is shown and it is also found to be phenomenally the same in the reference region $n_r$ (i.e., near the fluorescent substance). In addition, because almost the entire membrane is covered with analyte liquid when a test strip is used, it is assumed that the membrane is in a wet state. First, excitation light 71 is illuminated from an excitation light source L and passes through the transparent film 7. As a result, the excitation light 71 reaches the fluorescent labeling unit 2 of the membrane. The labeling unit 2 is present near the surface or inside of the membrane, and upon illumination with the excitation light, it emits fluorescence 72. Because the membrane is a porous body, the fluorescence is scattered by a solid phase constituting the porous body. After that, some of the scattered fluorescence reaches the interface with an external environment (air) A. However, when the membrane is wet with water, because the refractive index of water (analyte liquid) is larger than that of the external environment (air) A, the incident fluorescence with an incident angle larger than the critical angle is totally reflected and progresses in a direction returning to the inside of the membrane, and also scattered by the solid phase of the membrane, and thus it propagates inside the membrane (totally reflected light 73). The refractive index of an external environment (air) is evaluated to be 1.0 or so. Meanwhile, fluorescence with an incident angle smaller than the critical angle is released to the external environment A (emitted light 74 [see, FIG. 4]). Thus, on the interface between the membrane and the external environment, the incident fluorescence having an incident angle larger than the critical angle is totally reflected and scattered by the solid phase of the membrane, and thus it propagates inside the membrane, while the incident fluorescence having an incident angle smaller than the critical angle is released to the external environment A, yielding light illumination from entire membrane. The descriptions given above are based on a simplified model and the behavior of the light inside or outside the membrane may not necessarily correspond to them. However, the entire membrane typically exhibits light according to the mechanism described above. In addition, since analyte liquid used for fluorescence immunochromatography is liquid in which salts, proteins, surface active agents, or the like are dissolved in water and they have a higher refractive index than water, the refractive index of liquid phase is always higher than the refractive index of the air even when the analyte liquid is used, and therefore the same phenomenon as the above occurs. Accordingly, even when a line-shape fluorescence emission occurs in the test region (fluorescent labeling unit) $n_t$, light emission is spread to the peripheral region so that the light emission from the line appears to be relatively smeared or cloudy (see, FIG. 6).

Figure 3:
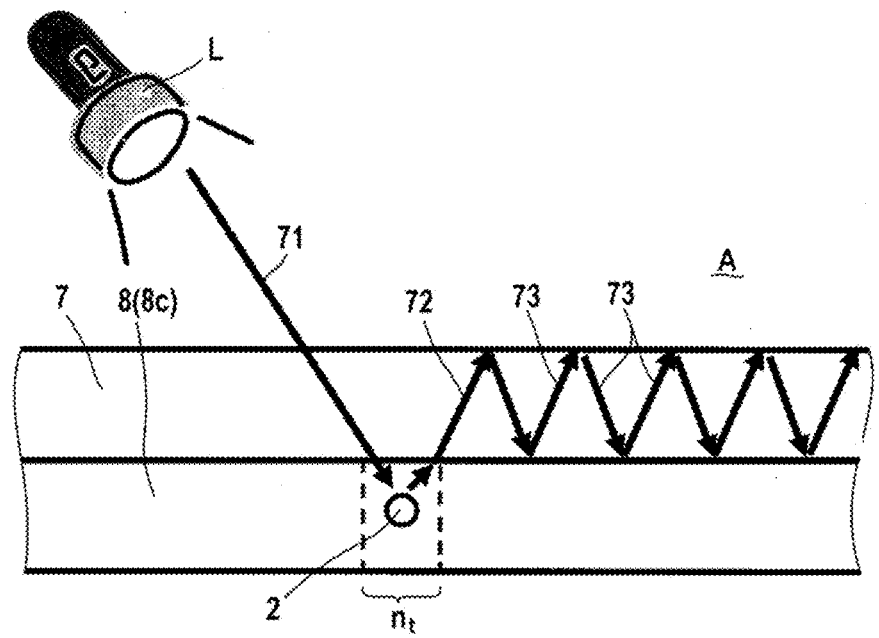
FIG. 3 is a diagram schematically illustrating reflection mechanism of excitation light and fluorescence according the fluorescence immunochromatography of the invention based on a cross section of the membrane.

Meanwhile, according to the invention, a specific transparent film 7 is applied to the membrane main body (see, FIG. 3), in which the film having a higher refractive index than that of the analyte liquid at a specific wavelength condition is used (see, Formula (1) above). The embodiment illustrated in FIG. 3 is the same as that of FIG. 4 in that the excitation light 71 is illuminated from the excitation light source L and received by the labeling unit 2 to emit the fluorescence 72, which is then scattered by the solid phase constituting the porous body of the membrane. After that, some of the scattered fluorescence 72 reaches the interface with the transparent film. However, since the transparent film 7 is present on the external surface of the membrane 8c and it has a higher refractive index than that of the analyte liquid, the fluorescence 72 is incident toward the film 7. After that, some of the fluorescence 72 further reaches the interface with the external environment A. However, because the refractive index of the transparent film is higher than that of the air so that it is totally reflected (reflected light 73) to be remained inside the film without being released to the external environment A when the incident angle is larger than the critical angle. In a lower direction, because the refractive index of the transparent film is still higher than that of the analyte liquid so that the reflected light 73 is totally reflected to be remained inside the film, and then propagated by having the film as a waveguide. In such case, unlike the membrane, since the reflected light 73 propagates without causing absorption or scattering of light in the transparent film, once totally reflected fluorescence is not released from the film surface to the external environment A, and thus the visibility of fluorescence emission near the fluorescent substance of the membrane 8c is maintained. As a result, the light emitting line in the test region $n_t$ is maintained in clear state without being suppressed by light emission or color exhibition near it, and therefore favorable detection can be achieved (see, FIG. 5).

Further, the excitation light 71 illuminated from the excitation light source L is incident on the transparent film 7 or reflected on the surface of the transparent film 7. While the excitation light 71 incident on the transparent film 7 passes through the transparent film 7 and is incident on the membrane 8c, some of the excitation light 71 is totally reflected on the interface of the membrane 8c of the transparent film 71. In addition, some of the excitation light 71 incident on the membrane 8c may contribute to generation of the fluorescence 72 while some of it does not contribute to generation of fluorescence as being scattered in the membrane 8c.

Further, after the excitation light scattered in the membrane 8c is incident to the transparent film 7, it may either pass through the transparent film 7 and released from the surface of the transparent film 7 or is totally reflected on the transparent film and released from the end face of the transparent film 7. In this regard, as described below, it is possible to detect only fluorescence by removing the excitation light released from the transparent film by way of installing a filter for selectively transmitting fluorescence immediately before a detector.

Herein, some of the fluorescence generated by the excitation of fluorescent substance in the reference region or test region of the membrane 8c is scattered inside the membrane 8c, while the remaining fluorescence is incident to the transparent film 7. The fluorescence incident to the transparent film 7 passes through the film and may be detected by the detector, when the incident angle of the fluorescence is smaller than the critical angle. However, when the incident angle of some of the fluorescence is larger than the critical angle, total reflection repeatedly occurs within the transparent film 7 and then it is released from the end face of the transparent film to outside. As described above, because the fluorescence intensity of the transparent film 7 is lowered by applying the transparent film 7 on the membrane 8c, it is possible to increase the fluorescence intensity of the reference region or the test region relatively higher than other region of the transparent film.

According to the fluorescence immunochromatography of the invention, the light transmittance of the transparent film 7 is, although not particularly limited, preferably 80% or more of the transmittance of the excitation light at maximum wavelength ($T_{Fe}$) and the transmittance of the fluorescence at maximum wavelength ($T_{Ff}$), or more preferably 90% or more of them. When the light transmittance is lower than that, a loss may be caused by absorption of the excitation light and fluorescence by film to lower the detection sensitivity.

The thickness of the transparent film is, although not particularly limited, preferably between 1 μm and 1 mm, and more preferably from 20 μm to 1 mm.

The contact angle of the transparent film to water is 50° or more. When the contact angle is less than 50°, the film may be easily impregnated by analyte liquid instead of permeating the membrane, and thus amount of the analyte liquid which moves along the interface between the membrane and the film is increased, leading to lower sensitivity.

Examples of the material of the transparent film include polyvinylidene fluoride, cellulose acetate, polymethyl methacrylate, polypropylene, nylon, polyethylene, polyvinyl chloride, polystyrene, polyvinylidene chloride, and polyethylene terephthalate.

Hereinafter, examples of the refractive index and contact angle of the transparent film consisting of the materials described above are given, but it is evident that the invention is not construed as being limited to them. Further, the contact angles described in {Table A} are measured based on the JIS R3257 (1999).

TABLE A

| Materials | Refractive index (wavelength: 542 nm) | Contact angle [deg] |
|---|---|---|
| Polyvinylidene fluoride | 1.42 | 82 |
| Cellulose acetate | 1.46-1.50 | 50-55 |
| Polymethyl methacrylate | 1.49 | 62 |
| Polypropylene | 1.49 | 91 |
| Nylon | 1.53 | 70-77 |
| Polyethylene | 1.53 | 88 |
| Polyvinyl chloride | 1.53 | 87 |
| Polystyrene | 1.6 | 84-91 |
| Polyvinylidene chloride | 1.61 | 80 |
| Polyethylene terephthalate | 1.66 | 77-80 |

Further, unless specifically described otherwise, the refractive index indicates the value at a temperature of 20° C. It is also the same for other optical properties such as transmittance, unless specifically described otherwise.

As used herein, the expression "attachment" for "attachment of the membrane to the film" described in the invention indicates a direct contact between the film and the membrane. However, as a constitution other than those described above, the film and the membrane may be attached to each other by way of adhesives. For such case, the analyte liquid flows along the interface between the adhesives and the membrane. However, it is actually difficult to have a gap between them because the gap between the film and the membrane is filled by the adhesives. Thus, when the light transmittance of the adhesives is excellent, the contact angle of the adhesives may be smaller than that of the film and there will be no case in which the analyte liquid is spread over the interface. In addition, since an adhesive layer generally has a thickness of several μm or so and the film thickness is not as even as the film, the fluorescence incident on the adhesive layer may be weakened by interference by each other during a total reflection process within a waveguide or it may escape from the adhesive layer. In case of escape, some of the fluorescence is released from an end part of the film based on a waveguide effect of the film, and thus it does not cause any problem for the fluorescence measurement. Thus, when the film and the membrane are attached to each other by way of adhesives, transparent adhesives having a high light transmittance are preferably used. Adhesives having a refractive index higher than the membrane or the analyte liquid are also preferably used.

Preferred examples of the adhesive layer include transparent acrylic adhesives and transparent epoxy adhesives. Preferred examples of the transparent acrylic adhesives and transparent epoxy adhesives include those having a refractive index of between 1.4 and 1.5. Further, with regard to the relation between the refractive index of the film and the refractive index of the adhesives, to inhibit the escape of the light incident on the film to the adhesive layer, it is preferable that the refractive index of the film be higher than the refractive index of the adhesives. Further, it is preferable that the refractive index of the adhesives be higher than the refractive index of analyte liquid.

Further, since the reactivity of an antibody is lowered when components contained in the adhesives are released therefrom, it is preferable that the adhesives should not or hardly contain water-soluble and releasable components.

[Meaning of Technical Expressions]

For clarification of the technical expressions used in the specification, the target substance 1 (although the reference numerals and symbols are denoted in FIG. 1, the invention is not construed as being limited thereto) is a substance as an object for detection by lateral flowmetry, and it has the same meaning as the test substance in an analyte. Each of the binding substances 2b and 3b indicates a substance having binding property to the target substance and capturing substance, respectively, and it is preferably a biomolecule. The labeling particles 2a and 3a introduced with a labeling substance (not illustrated) are referred to as the labeling units 2 and 3. However, in broad sense, the term "labeling particles" may be also used to have a meaning including a labeling unit. Meanwhile, those immobilized to the membrane in test region and capturing the labeling unit 2 by way of the target substance 1 are the test use capturing substance 4. Meanwhile, those immobilized to the membrane in reference region are the reference use capturing substance 5, and the labeling unit 3 is bound thereto without being mediated by the target substance 1.

As described herein, the expression "prepare" broadly means obtaining pre-determined products or materials by purchase or the like, in addition to producing them for preparation. Thus, "preparing a membrane" means that it is only required that the membrane is presently available at hand, and a method of obtaining or a method of production is not limited at all.

[Fluorescent Silica Particles]

As for the labeling particles (labeling unit) 2 and 3 used for the fluorescence immunochromatography of the invention, the labeling particles 2a and 3a such as fluorescent silica particles, fluorescent latex particles, and semi-conductor nanoparticles may be used in combination with the binding biomolecules 2b and 3b. According to the invention, it is particularly preferable to use the fluorescent silica particles.

Method for producing the fluorescent silica particles is not particularly limited, and silica particles obtained by any arbitrary production method can be used. Examples of the method include a sol-gel method described in Journal of Colloid and Interface Science, 159, 150-157 (1993).

According to the invention, it is particularly preferable to use silica particles containing functional compounds, which are obtained by a method of producing colloid silica particles containing fluorescent pigment compounds as described in WO 2007/074722 A1. Specific examples of the functional compounds include a fluorescent pigment compound, a light absorbing compound, a magnetic compound, a radioactive-labeled compound, and a pH sensitive pigment compound.

Specifically, the silica particles containing functional compounds can be prepared by reacting the functional compounds with a silane coupling agent and performing polycondensation of a product obtained through a covalent bond, ionic bond, or other chemical bonds or by adsorption with one or more of silane compounds to form a siloxane bond. Accordingly, the silica particles consisting of the organosiloxane component and siloxane component that are bound to each other via siloxane bond are obtained.

As a preferred mode of producing the silica particles containing the functional compound, production can be made by reacting the functional compound having or provided with an active group such as an N-hydroxysuccinimide (NHS) ester group, a maleimide group, an isocyanate group, an isothiocyanate group, an aldehyde group, a para-nitrophenyl group, a diethoxy methyl group, an epoxy group, and a cyano group with a silane coupling agent having a substituent group which reacts with those active groups (e.g., an amino group, a hydroxy group, and a thiol group), and condensing and polymerizing the product obtained by forming a siloxane bond after forming a covalent bond with one or more types of silane compounds.

The following example relates to a case in which APS and tetraethoxy silane (TEOS) are used as a silane coupling agent and a silane compound, respectively.

Specific examples of the functional compound having or provided with an active group (fluorescent substance) may include NHS ester group-containing fluorescence dye substances such as 5- (and -6)-carboxytetramethylrhodamine-succinimidyl NHS ester (trade name, manufactured by emp Biotech GmbH), DY550-NHS ester or DY630-NHS ester represented as follows (trade name for both, manufactured by Dyomics GmbH).

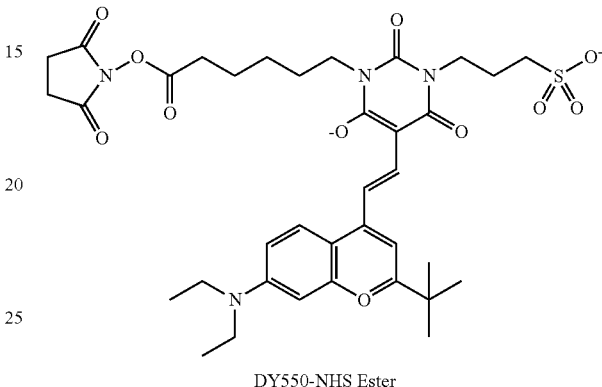

DY550-NHS Ester

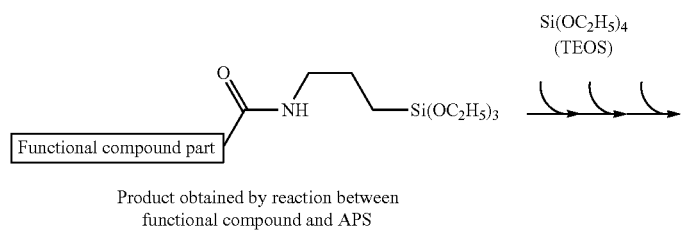

Product obtained by reaction between functional compound and APS

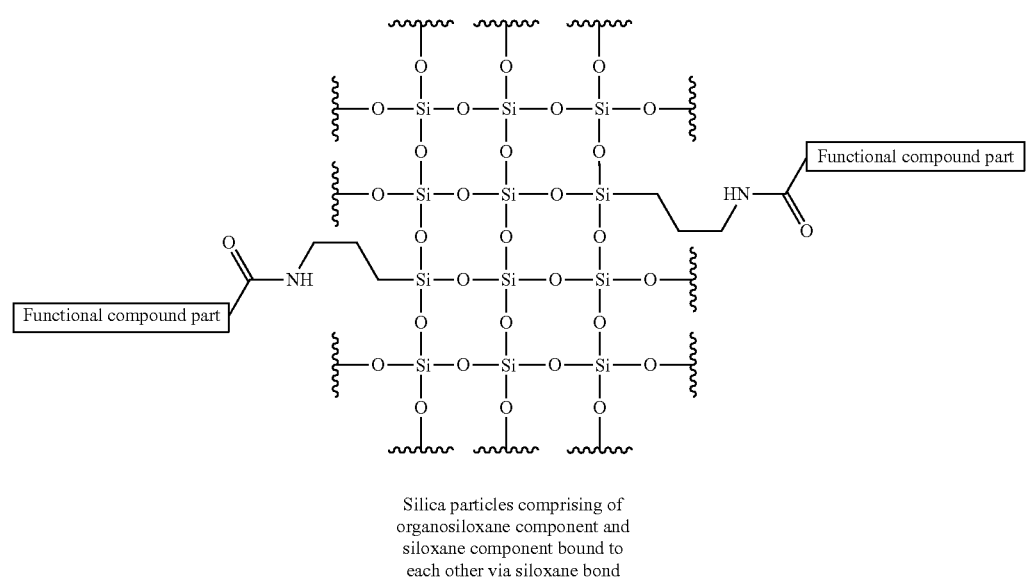

Silica particles comprising of organosiloxane component and siloxane component bound to each other via siloxane bond

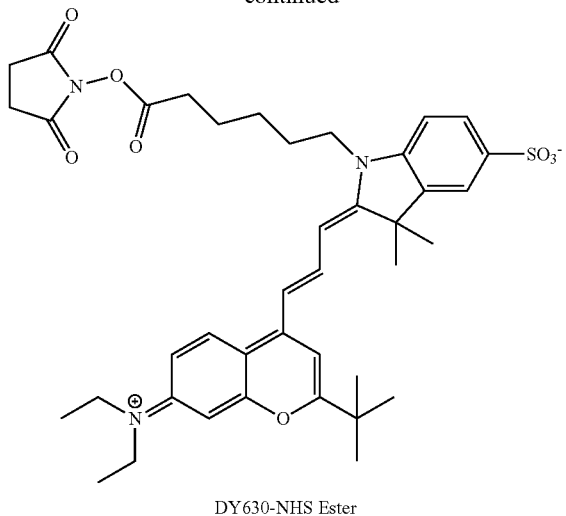

DY630-NHS Ester

Examples of substituent group-containing silane-coupling agent include an amino group-containing silane-coupling agent such as γ-aminopropyltriethoxysilane (APS), 3-[2-(2-aminoethylamino)ethylamino]propyltriethoxysilane, N-2-(aminoethyl)-3-aminopropylmethyldimethoxysilane, and 3-aminopropyltrimethoxysilane. Among them, APS is preferable.

The silane compound to be condensed and polymerized is not particularly limited, and examples thereof include TEOS, γ-mercaptopropyltrimethoxysilane (MPS), γ-mercaptopropyltriethoxysilane, γ-aminopropyltriethoxysilane (APS), 3-thiocyanatopropyltriethoxysilane, 3-glycidyloxypropyltriethoxysilane, 3-isocyanatopropyltriethoxysilane, and 3-[2-(2-aminoethylamino)ethylamino]propyl-triethoxysilane. Among them, TEOS is preferable from the point of view of forming a siloxane component to be contained in the silica particle, and besides MPS, and APS are preferable from the point of view of forming an organosiloxane component to be contained in the silica particle.

According to the production as described above, spherical or almost spherical silica particles can be prepared. Meanwhile, the almost spherical particles mean particles having a major axis/minor axis ratio of 2 or less.

For obtaining silica particles having a desirable average particle diameter, it is possible to remove particles having an excessively large particle diameter or an excessively small particle diameter by ultrafiltration by using an ultrafiltration membrane such as YM-10 or YM-100 (trade names, all manufactured by Millipore Corporation) or by recovering only a supernatant or precipitates after performing centrifugal separation with suitable acceleration of gravity.

As a biomolecules to be combined or absorbed on the surface of silica particles, there includes antigens, antibodies, DNAs, RNAs, sugars, polysaccharides, ligands, receptors, peptides, chemical substances and the like. Here, the term "ligand" means a substance capable of specifically binding to a protein, and examples thereof include substrates capable of binding to enzyme, coenzymes, regulatory factors, hormones, neurotransmitters, and the like, and thus, the ligands include low-molecular weight molecules as well as a polymer substances.

The average diameter of the fluorescent silica particles is preferably 1 nm to 1 μm, more preferably 20 nm to 500 nm, for improvement of cell detection sensitivity.

In the present invention, the average diameter is an average diameter of the circle (average circle-equivalent diameter) obtained by measuring the total projected area of 100 pieces of randomly-selected labeling reagent silica particles for example in an image obtained under transmission electron microscope (TEM) or scanning electron microscope (SEM) using an image processing equipment, dividing the total area with the number of the labeling reagent silica particles (100 pieces), and determining the circle having an area equivalent to that.

Further, the average particle diameter indicates an average particle diameter of particles consisting of only primary particles, which is different from the "particle size according to a dynamic light scattering method" described below having a concept including secondary particles formed by aggregation of primary particles.

As described herein, the "particle size according to the dynamic light scattering method" is measured by the dynamic light scattering method, and it is a concept including secondary particles formed by aggregation of primary particles as well as primary particles, different from average particle diameter, and it is an indicator for evaluating dispersion stability of complex particles described above.

Examples of a device for measuring particle size according to the dynamic light scattering method include Zetasizer Nano (trade name, manufactured by Malvern Instruments Ltd.). According to the method, fluctuation in light scattering intensity over time that is caused by light scatterers such as particulates is measured, the speed of the light scatterers in Brownian motion is calculated based on an autocorrelation function, and the particle size distribution of the light scatterers is determined based on the results.

The particles of the present invention preferably have monodispersion as a granular substance. The variation coefficient, so-called CV value, of the particle size distribution is not specifically limited, but preferably 10% or less, and more preferably 8% or less.

[Detection Method]

The method of detecting a target substance according to the immunochromatography of the invention is a method including concentrating on a determination part the migrating labeling reagent silica nanoparticles (labeling unit) 2 and 3 based on capillary phenomenon and performing the determination. It is preferably performed by immunochromatography or using a micro flow chip or the like. The labeling reagent silica nanoparticles may be preferably used as a labeling unit for lateral flowmetry. In addition, according to the method of detecting a target substance according to the invention, it is preferable to detect a target substance by using lateral flow type immunochromatography.

With regard to a method for producing the test strip, a sample pad, a conjugate pad, an antibody immobilizing membrane, and an absorption pad are overlaid in that order while both ends of each member are attached to the neighboring member such that they are overlapped with each other within a range of 1 to 5 mm (preferably, on a backing sheet) so as to easily cause capillary phenomenon between the respective members.

The fluorescence detection system for the immunochromatography preferably consists of at least (1) sample pad, a member impregnated with labeling reagent silica nanoparticles consisting of a fluorescent substance or labeling reagent silica nanoparticles for lateral flow (i.e., a conjugate pad), and a test strip consisting of an antibody immobilizing membrane and an absorption pad, and (2) an excitation light source.

According to the fluorescence detection system, from the viewpoint of detecting with the naked eye the fluorescence emitted from the labeling reagent silica nanoparticles (labeling units), it is preferable that excitation light source capable of emitting excitation light with a wavelength of 200 nm to 400 nm be used. Examples of the excitation light source include a mercury lamp, a halogen lamp, and a xenon lamp. According to the invention, excitation light illuminated from a laser diode or light emitting diode is particularly preferably used.

Further, the fluorescence detection system is preferably equipped with a filter for selectively transmitting light of specific wavelength from the excitation light source. Further, from the viewpoint of detecting only the fluorescence with the naked eye, it is more preferably equipped with a filter which is capable of removing the excitation light and transmitting only the fluorescence.

The fluorescence detection system may particularly preferably be provided with a photoelectric multiplier tube for collecting the fluorescence or a CCD detector. Accordingly, fluorescence with visually undeterminable intensity or wavelength can be detected, and further quantification of a tart substance can be made as its fluorescence intensity can be measured, enabling detection and quantification with high sensitivity.

The wavelength of the excitation light is preferably between 300 nm and 700 nm. The wavelength of the fluorescence is preferably a wavelength that can be recognized with the naked eye, i.e., preferably between 350 nm and 800 nm. Further, from the viewpoint of obtaining high visibility when observed with the naked eye, the wavelength is preferably between 530 nm and 580 nm. For such case, the wavelength of the excitation light is preferably between 500 nm and 550 nm for efficient generation of the fluorescence within the wavelength range described above.

From the viewpoint of easy handling by an unskilled individual and also of POCT (Point Of Care Testing), the test strip according to a preferred embodiment of the invention preferably has a housing (i.e., a casing) with an observation window made of plastic materials or the like which allows the detection line of the test strip to be observed with the naked eye. For example, the housing described in JP 2000-356638 A can be mentioned.

The above term "POCT" means a test for diagnosing a patient at possibly nearest place. Conventionally, a collected analyte like blood, urine, and tissues of lesion is sent to a central test lab of a hospital or a professional test center to obtain the data, and thus it takes a time (e.g. 1 day or more) to have a confirmed diagnosis. However, according to POCT, a fast yet accurate treatment can be made, based on the test information which is supplied in short time. From such point of view, it enables an urgent test or a test during operation at hospital, and thus it is highly needed at actual medical site, in particular.

According to the fluorescence immunochromatography of the invention, a relatively smeared or blurred fluorescence line due to the phenomenon of having entirely gleaming membrane can be suppressed or prevented even when the membrane is in a wet state. Accordingly, for the fluorescence immunochromatography, the determination can be made by quicker and more precise detection of the fluorescent line.

The present invention will be described in more detail based on examples given below, but the invention is not meant to be limited by these.

EXAMPLES

Preparation Example 1 (Preparation of Silica Nanoparticles)

2.9 mg of 5- (and -6)-carboxy tetramethylrhodamine•succinimidyl ester (trade name, manufactured by EMP Biotech GmbH) was dissolved in 1 mL dimethyl formamide (DMF). Then, 1.3 µL of APS was added thereto and the reaction was carried out for 1 hour at room temperature (24° C.).

600 µL of the resulting reaction liquid was admixed with 140 mL of ethanol, 6.5 mL of TEOS, 35 mL of distilled water, and 15 mL of 28% by mass ammonia water, and the reaction was allowed to occur at room temperature for 24 hours.

The reaction solution was centrifuged at a gravitational acceleration of 15,000×g for 30 minutes, and the supernatant was removed. 4 ml of distilled water was added to the precipitated silica particle for dispersion, and the dispersion was centrifuged again at a gravitational acceleration of 15,000×g for 20 minutes. Further, the washing operation was repeated twice additionally, for removal of the unreacted TEOS, ammonia and others contained in the silica nanoparticle dispersion, 1.71 g of silica nanoparticles having an average particle diameter of 173 nm were obtained. Yield ratio ca. 97%.

Preparation Example 2 (Preparation of Complex Particles of Silica Particles and an Antibody)

100 µL of dispersion solution (dispersion medium: distilled water) of silica particles (average particle diameter; 173 nm) containing rhodamine 6G at a concentration of 5 mg/mL, which had been used in Preparation example 1, was added with 775 µL of distilled water, 100 µL of an aqueous solution of sodium alginate with a concentration of 10 mg/mL (weight average molecular weight: 70,000), and 25 µL of an aqueous ammonia solution with a concentration of 28% by weight, and then slowly stirred for 1 hour at room temperature (24° C.). The obtained colloid was subjected to centrifugation for 30 minutes with an acceleration of 12,000×g, and then the supernatant was removed. Distilled water (875 µL) was added thereto and the particles were re-dispersed. Subsequently, 100 µL of an aqueous solution of sodium alginate with a concentration of 10 mg/mL was added and stirred well using a stirrer followed by addition of 25 µL of an aqueous ammonia solution with a concentration of 28% by weight and slowly stirred for 1 hour. The resulting colloid was subjected to centrifugation for 30 minutes with an acceleration of 12,000×g, and then the supernatant was removed. After adding 1 mL of distilled water, particles were dispersed. Centrifugal isolation and dispersion with distilled water were repeated twice in the same manner as above for washing the particles, which were than dispersed in 200 µL of distilled water to obtain colloid of complex particles of the silica particles containing rhodamine 6G/aliginic acid (yield: 2.5 mg/mL×200 µL).

To the colloid of complex particles of the silica particles containing rhodamine 6G/aliginic acid, 100 µL of 0.5 M 2-morpholinoethanesulfonic acid, monohydrate buffer (pH 6.0), 395 µL of distilled water, 230 µL of an aqueous solution of 50 mg/mL NHS(N-hydroxysuccinimide), and 75 µL of 19.2 mg/mL aqueous solution of EDC (1-ethyl-3-(3-dimethylaminopropyl)carbodiimide) were added in order followed by mixing for 10 min.

The colloid was subjected to centrifugation for 10 minutes with an acceleration of 12,000×G, and the supernatant was removed. Then, 480 µL of 50 mM $KH_2PO_4$ (pH 7.0) was added for dispersing the particles. 20 µL (5.8 mg/mL) of an anti hCG antibody (Anti-hCG clone codes/5008, manufactured by Medix Biochemica) was also added, and by slow mixing at room temperature for 30 min, the silica nanoparticles were linked with the anti hCG antibody via covalent bond.

Subsequently, the colloid was subjected to centrifugation for 10 minutes with an acceleration of 12,000×G, and the supernatant was removed. Then, 1 mL of 50 mM $KH_2PO_4$ (pH 7.0) was added for dispersing the particles. After the centrifugation for 10 minutes with an acceleration of 12,000×G, the supernatant was removed. Then, 1 mL of 50 mM $KH_2PO_4$ (pH 7.0) was added for dispersing the particles. After the centrifugation for 10 minutes with an acceleration of 12,000×G, the supernatant was removed. 1 mL of 50 mM $KH_2PO_4$ (pH 7.0) was added for dispersing the particles, and then 1 mL of colloid of complex particles of the silica particles and the anti hCG antibody with a concentration of 0.5 mg/mL was obtained.

Example 1: Comparative Example 1 (Manufacture and Evaluation of the Test Strip for Immunochromatography)

The colloid of the complex particles that had been obtained from Preparation example 1 (240 µL) and 50 mM $KH_2PO_4$ (pH 7.0, 560 µL) were admixed with each other. The resulting mixture (800 µL) was uniformly coated on Glass Fiber Conjugate Pad (GFCP, manufactured by MILLIPORE) (8×150 mm). After drying overnight at room temperature under reduced pressure in a desiccator, a conjugate pad including the complex particles which had been obtained from Preparation example 2 was produced.

Next, an antibody immobilizing membrane was produced as follows.

Near the center of the membrane (length: 25 mm, trade name: Hi-Flow Plus120 membrane, manufactured by MILLIPORE) (about 12 mm from the end of the membrane), a solution ((50 mM $KH_2PO_4$, pH 7.0)+5% sucrose) containing anti-hCG antibody (alpha subunit of FSH (LH), clone code/ 6601, manufactured by Medix Biochemica) in an amount of 1 mg/mL was coated in a coating amount of 0.75 µL/cm to give a test line with width of about 1 mm.

Subsequently, as a control line with width of about 1 mm, a solution ((50 mM $KH_2PO_4$, pH 7.0), sugar free) containing Anti-Mouse IgG antibody (Anti Mouse IgG, Dako Inc.) in an amount of 1 mg/mL was coated in a coating amount of 0.75 µL/cm followed by drying for 30 min at 50° C. A distance between a test line and a control line was 3 mm.

The sample pad (Glass Fiber Conjugate Pad (GFCP), manufactured by MILLIPORE), the conjugate pad, the antibody immobilizing membrane, and the absorption pad (Cellulose Fiber Sample Pad (CFSP), manufactured by MILLIPORE) were assembled in order on a backing sheet (trade name; AR9020, manufactured by Adhesives Research).

Subsequently, a PET film (TEIJIN TETORON (registered trademark) film G2P2 (manufactured by Teijin DuPont Films)) was attached thereto such that it covered a region starting from a spot at 1.4 mm away from the end of the sample pad to a spot at 1.2 mm away from the end of the absorption pad.

Subsequently, it was cut to have a strip shape with a width of 5 mm and a length of 60 mm to give a test strip 101 having the constitutions illustrated in FIGS. 1A and 1B.

Furthermore, each constitutional member was attached such that both ends thereof are overlapped by 2 mm or so with a neighboring member as illustrated in FIG. 2A and FIG. 2B (ditto for the following).

A test strip 102 was manufactured in the same manner as Example 1 except that a polypropylene film (GL-422-CLEAR, manufactured by G & L) is used as a film.

As the Comparative example, a test strip c11 was manufactured in the same manner as Example 1 except that no film is attached.

Quick Determination of Recombinant hCG

Recombinant hCG (prepared by Scripps Laboratories) adjusted to 2 IU/L was prepared, and the refractive index thereof was measured. As a result, the refractive index was found to be 1.36. Subsequently, the recombinant hCG liquid was added dropwise in an amount of 100 µL to the sample pads of the test strips which had been manufactured in Example 1, Example 2, and the Comparative example. After lapses of 0, 5, 10, 15, 20, 25, and 30 minutes, respectively, the test line determination was performed by using a fluorescence reader. As described herein, the fluorescence reader indicates a device consisting of a laser diode with a wavelength of 532 nm and an optical filter, by which the laser diode illuminates a line region of membrane and only the fluorescence emitted from fluorescent particles is observed by monitoring the line through an optical film.

Figure 5:
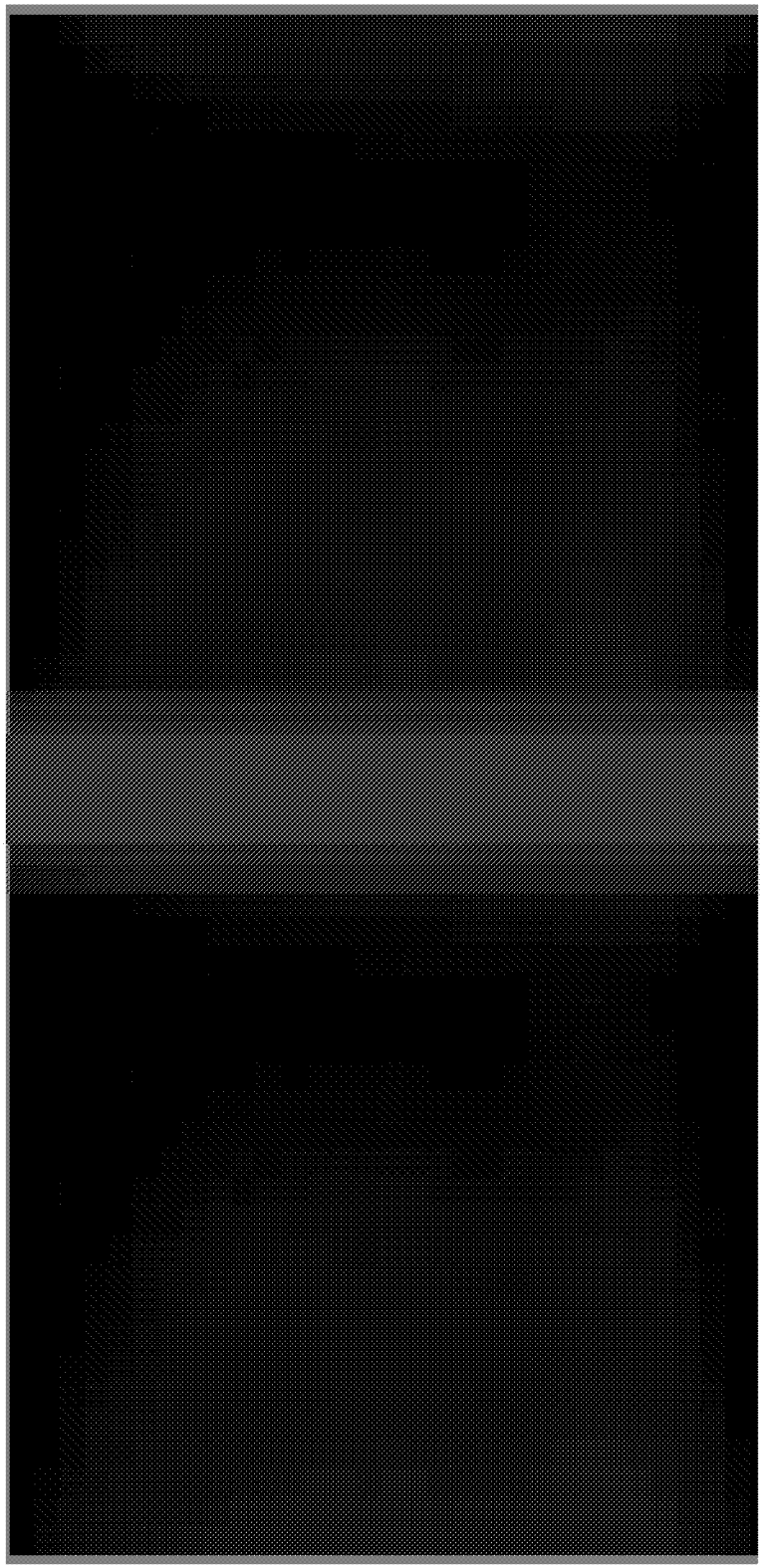
FIG. 5 is a photographic image as a substitute for figure to illustrate an enlarged image of an exemplary fluorescent line obtained from the fluorescence immunochromatography of the invention.
Figure 6:
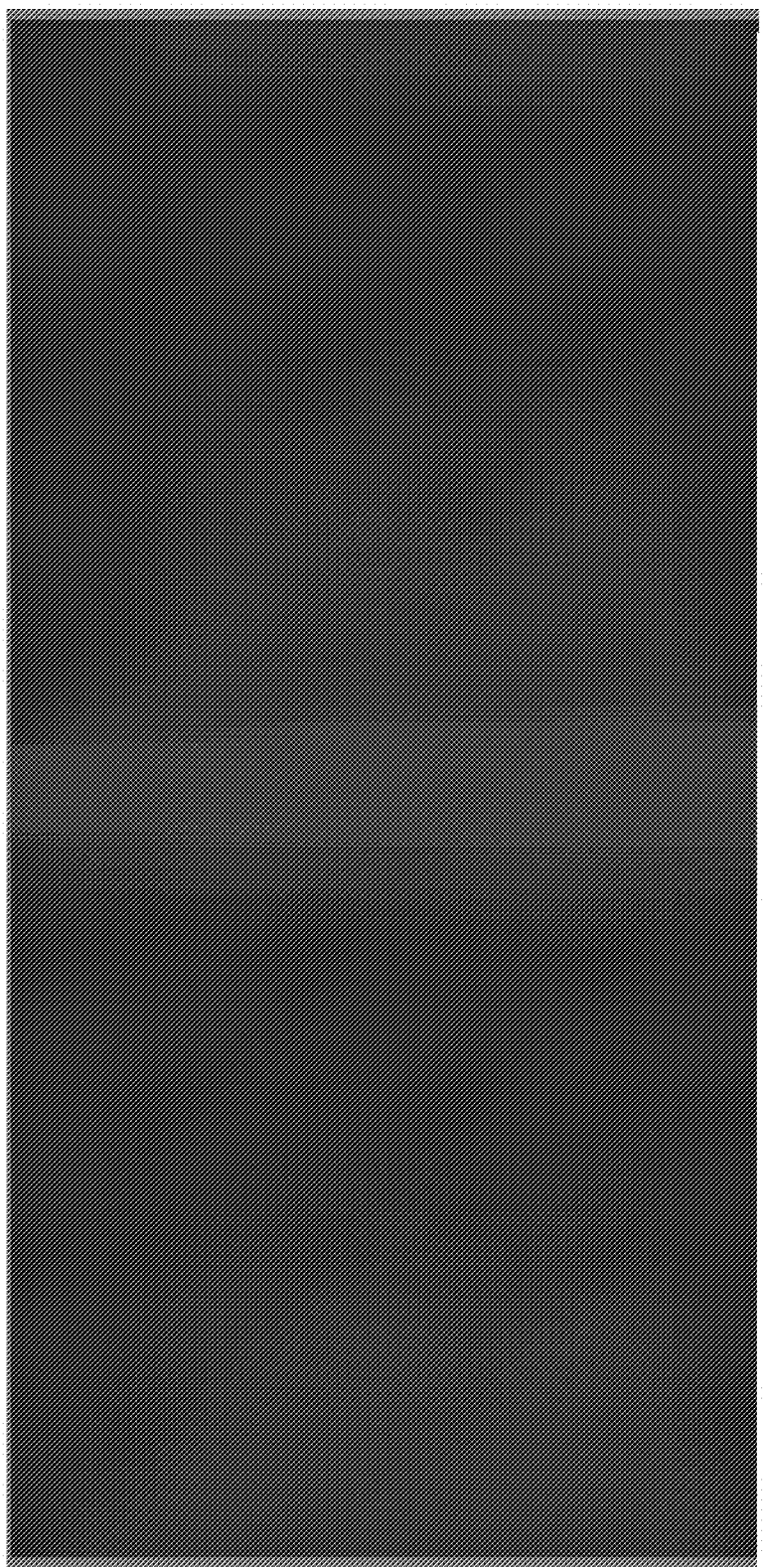
FIG. 6 is a photographic image as a substitute for figure to illustrate an enlarged image of an exemplary fluorescent line obtained from conventional fluorescence immunochromatography.

The results of determination are shown in Table 1. In the drawings, "+" represents a visible test line while "−" represents a non-visible test line. In the Comparative example, it took 30 minutes until the fluorescence from a test line was confirmed. However, it took only 10 minutes and 15 minutes for Example 1 and Example 2, respectively. These results suggest that, by applying a film, the test line determination can be made within a short time. Further, since the positive test line was shown in shorter time in Example 1 compared to Example 2, it is found that use of a PET film having higher difference in a refractive index to water can shorten the determination time compared to that of a polypropylene film. FIG. 5 is an enlarged image of Example 1 at a time point of 30 minutes and FIG. 6 is an enlarged image of the Comparative example at a time point of 30 minutes.

TABLE 1

| Test piece | | 101 | 102 | c11 |
|---|---|---|---|---|
| Transparent film | | PET | PP | None |
| Excitation light | $\lambda^e$ | 532 nm | 532 nm | 532 nm |
| Refractive index | $n_{Fe}$ | 1.66*[2] | 1.49*[2] | ca. 1.0 *[1] |
| | $n_{We}$ | 1.36 | 1.36 | 1.36 |
| Fluorescence | $\lambda^f$ | 555 nm | 555 nm | 555 nm |
| Refractive index | $n_{Ff}$ | 1.66*[2] | 1.49*[2] | ca. 1.0 *[1] |
| | $n_{Wf}$ | 1.36 | 1.36 | 1.36 |
| Time [min] | 0 | − | − | − |
| | 5 | − | − | − |
| | 10 | + | − | − |
| | 15 | + | + | − |
| | 20 | + | + | − |
| | 30 | + | + | + |

PET: polyethylene terephthalate
PP: polypropylene
*[1] refractive index of the air was estimated to be about 1.0
*[2] reference was made to Table A Example 2: Comparative Example 2 (Evaluation of Detection Sensitivity for Recombinant hCG)

Recombinant hCG (prepared by Scripps Laboratories) diluted to suitable concentration was prepared and the refractive index thereof was measured. As a result, the refractive index was found to be 1.36. Subsequently, the recombinant hCG (prepared by Scripps Laboratories) solution which had been diluted to suitable concentration was added dropwise to the sample pad of the test strip which had been manufactured in Example 1 and Comparative example 1. After a lapse of 10 minutes, the test line determination was performed by using a fluorescence reader (Test subjects No. 101 and 102 correspond to the Examples, and Test subject No. c11 corresponds to the Comparative example).

The results of determination are shown in Table 2. According to the test c21, at least 5 IU/L was required for determination of a test line. However, according to the test 201 and the test 202, the determination of the test line was made as low as 1 IU/L and 2 IU/L, respectively. Those results suggest that, by applying a film, an antigen at lower concentration can be detected with a determination time of 10 minutes. Further, because an antigen of even lower concentration can be detected by test 201 compared to test 202, it is found that the detection sensitivity is improved when a PET film having a higher difference in a refractive index to water is used instead of a polypropylene film.

TABLE 2

| Test piece | | 101 | 102 | c11 |
|---|---|---|---|---|
| Transparent film | | PET | PP | None |
| Antigen | 0 | − | − | − |
| concentration | 0.5 | − | − | − |
| [IU/L] | 1 | + | − | − |
| | 2 | + | + | − |
| | 5 | + | + | + |
| | 10 | + | + | + |
| | 20 | + | + | + |

Having described the present invention as according to the present embodiments, it is our intention that the invention not be limited by any of the details of the description, unless otherwise specified, but rather be construed broadly within its spirit and scope as set out in the accompanying claims.

EXPLANATIONS OF LETTERS OR NUMERALS

1 Target substance (analyte substance)
2 Fluorescent labeling unit
  2a Fluorescent particulates
  2b Test use binding substance
3 Fluorescent labeling unit
  3a Fluorescent particulates
  3b Reference use binding substance
4 Test use capturing substance
5 Reference use capturing substance
6 Casing
  61 Opening for detection
  62 Opening for introducing analyte
  6a Upper casing
  6b Lower casing
7 Transparent film
80 membrane main body
  8a Sample pad
  8b Conjugate pad
  8c Membrane
  8d Absorption pad
10 Test strip
100 Test stick
$n_r$ Reference area (close to fluorescent substance)
$n_t$ Test area (close to fluorescent substance)
L Lateral flow direction
S Analyte

The invention claimed is:

1. A fluorescence immunochromatography method carried out by illuminating a fluorescent substance in a membrane with excitation light and detecting fluorescence emitted from the fluorescent substance, the fluorescence immunochromatography method comprising the steps of:
  applying a sample to a test strip having a membrane and a transparent film attached to the surface of the membrane,
    wherein the transparent film satisfies Formula (1)

$$n_{Ff} < n_{Wf} \quad \text{Formula (1)}$$

($n_{Ff}$: refractive index of transparent film at wavelength $\lambda^f$ of the fluorescence)
    ($n_{Wf}$: refractive index of analyte liquid at wavelength $\lambda^f$ of the fluorescence), and
    wherein the membrane contains a fluorescent labeling reagent which binds to target substance contained in the sample;
  binding the fluorescent labeling reagent to the target substance;
  immobilizing the fluorescent labeling reagent bound to the target substance in the membrane;
  detecting the presence of target substance by illuminating the fluorescent labeling reagent bound to the target substance in the membrane with excitation light through the transparent film, thereby bringing fluorescence components into a guided wave within the transparent film,
    wherein the fluorescence components are included in the fluorescence incident to the transparent film and have an incident angle exceeding a critical angle, and
    wherein the fluorescence is wave guided by virtue of the fluorescence components being totally reflected on an interface between the transparent film and the air and on the surface of the membrane; and
  detecting another fluorescence components not exceeding the critical angle, wherein the another fluorescence components are included in the fluorescence emitted from the fluorescent substance, the detection being made by virtue of the fluorescence components passing through the film.

2. The fluorescence immunochromatography method according to claim 1, wherein the transparent film further satisfies Formula (2)

$$n_{Ff} > n_{Wf} + 0.1 \quad \text{Formula (2)}$$

($n_{Ff}$ and $n_{Wf}$ have the same meanings as defined in Formula (1)).

3. The fluorescence immunochromatography according to claim 1, wherein both the light transmittance ($T_{Fe}$) for wavelength $\lambda^e$ of the excitation light and the light transmittance ($T_{Ff}$) for wavelength $\lambda^f$ of the fluorescence of the transparent film are 80% or higher.

4. A fluorescence immunochromatography according to claim 1, wherein the contact angle of water on the transparent film is 50° or more.

5. The fluorescence immunochromatography according to claim 1, wherein fluorescent silica particles containing the fluorescent substance introduced to silica are used.

6. The fluorescence immunochromatography according to claim 1, wherein the wavelength $\lambda^e$ of the excitation light is between 300 nm and 700 nm, and wherein the wavelength $\lambda^f$ of the fluorescence is between 350 nm and 800 nm.

7. The fluorescence immunochromatography according to claim 1, wherein the wavelength $\lambda^e$ of the excitation light is between 500 nm and 550 nm, and wherein the wavelength $\lambda^f$ of the fluorescence is between 530 nm and 580 nm.

8. The fluorescence immunochromatography according to claim 1, wherein the fluorescence incident to the transparent film and diffused therein is totally reflected on the interface between the transparent film and the air and on the interface between the transparent film and the membrane so that the transparent film becomes a waveguide, which suppresses the fluorescence from being diffused in the membrane and increases detectability of the fluorescence near the fluorescent substance.

9. The fluorescence immunochromatography according to claim 1, wherein the excitation light is illuminated from a laser diode or a light emitting diode while a device for detecting only the fluorescence by removing the excitation light using an optical filter is used.

10. The fluorescence immunochromatography according to claim 1, wherein the detection determination is made within 5 minutes.

* * * * *